United States Patent [19]

Forse et al.

[11] Patent Number: 5,397,778
[45] Date of Patent: Mar. 14, 1995

[54] ENTERAL FORMULATIONS FOR TREATMENT OF INFLAMMATION AND INFECTION

[75] Inventors: R. Armour Forse, Brookline; Sambasiva Chavali, Boston, both of Mass.

[73] Assignee: New England Deaconess Hospital Corporation, Boston, Mass.

[21] Appl. No.: 228,599

[22] Filed: Apr. 15, 1994

Related U.S. Application Data

[63] Continuation-in-part of Ser. No. 201,682, Feb. 25, 1994.

[51] Int. Cl.[6] .............................................. A61K 31/38
[52] U.S. Cl. .................................. 514/198; 424/195.1; 424/DIG. 13; 426/804; 426/810; 514/464; 514/468; 514/783; 514/825; 514/886; 514/887; 514/904; 514/905
[58] Field of Search ................... 424/195.1, DIG. 13; 514/198, 464, 468, 783, 825, 886, 887, 904, 905; 426/804, 810

[56] References Cited

U.S. PATENT DOCUMENTS

| | | | |
|---|---|---|---|
| 3,901,875 | 8/1975 | Park | 424/195.1 |
| 3,920,440 | 11/1975 | Takaoka et al. | 71/88 |
| 4,317,816 | 3/1982 | Arichi et al. | 424/195.1 |
| 4,339,442 | 7/1982 | Takemoto et al. | 536/4.1 |
| 4,375,480 | 3/1983 | Soma | 514/844 |
| 4,427,694 | 1/1984 | Benecke et al. | 424/195.1 |
| 4,442,092 | 4/1984 | McBrayer | 424/195.1 |
| 4,501,734 | 2/1985 | Tanaka et al. | 424/195.1 |
| 4,649,206 | 3/1987 | Namiki et al. | 549/435 |
| 4,708,820 | 11/1987 | Namiki et al. | 426/542 |
| 4,722,941 | 2/1988 | Eckert et al. | 514/784 |
| 4,752,618 | 6/1988 | Mascioli et al. | 514/560 |
| 4,755,504 | 7/1988 | Liu | 514/26 |
| 4,767,626 | 8/1988 | Cheng | 424/195.1 |
| 4,774,229 | 9/1988 | Jordan | 514/25 |
| 4,774,343 | 9/1988 | Namiki et al. | 549/435 |
| 4,780,475 | 10/1988 | Cerra et al. | 514/561 |
| 4,803,153 | 2/1989 | Shibata et al. | 435/2 |
| 4,810,726 | 3/1989 | Bistrian et al. | 514/943 |
| 4,920,098 | 4/1990 | Cotter et al. | 514/23 |
| 4,966,893 | 10/1990 | Pang et al. | 514/54 |
| 4,981,844 | 1/1991 | Alexander et al. | 514/21 |
| 5,053,387 | 10/1991 | Alexander | 514/21 |
| 5,055,446 | 10/1991 | Alexander et al. | 514/23 |
| 5,166,139 | 11/1992 | Bombardelli et al. | 514/26 |
| 5,180,588 | 1/1993 | Shinmen et al. | 424/439 |
| 5,209,826 | 5/1993 | Ozaki et al. | 435/134 |
| 5,211,953 | 5/1993 | Shinmen et al. | 424/439 |
| 5,214,062 | 5/1993 | Mark et al. | 514/560 |
| 5,229,136 | 7/1993 | Mark et al. | 424/195.1 |
| 5,231,085 | 7/1993 | Alexander et al. | 514/44 |
| 5,260,336 | 11/1993 | Forse et al. | 514/560 |
| 5,270,335 | 12/1993 | Akimoto et al. | 514/470 |
| 5,273,965 | 12/1993 | Kensil et al. | 514/3 |

OTHER PUBLICATIONS

Sugano and Akimoto, (1993), "Sesamin: A Multifunctional Gift From Nature", Journal of Chinese Nutrition Socity, vol. 18, pp. 1–11.

Shimizu et al., (1993), "Studies on Desaturase Inhibitors of Polyunsaturated Fatty Acid Biosynthesis", Eds: A Sinclair and R. Gibson, American Oil Chemists' Society, pp. 37–41.

Hirose et al., (1991), "Inhibition of cholesterol absorption and synthesis in rats by sesamin", JOurnal of Lipid Research, vol. 32, pp. 629–638.

Shimizu et al., (1991), "Sesamin Is a Potent and Specific Inhibitor of $\Delta 5$ Desaturase in Polyunsaturated Fatty (List continued on next page.)

Primary Examiner—Ronald W. Griffin

[57] ABSTRACT

The present invention features saponin containing enteral formulations for treatment of infection and inflammation. These saponin containing formulations are particularly useful in conjunction with oils rich in $\omega 3$ polyunsaturated fatty acids such as fish oils and flax oil but also show benefits with $\omega 6$ rich oils such as borage oil, black currant seed oil, canola oil and rapeseed oil. These formulations may also contain a lignan from the sesamin family.

16 Claims, No Drawings

OTHER PUBLICATIONS

Acid Biosynthesis", *Lipids,* vol. 26, No. 7, pp. 512–516.

Salerno et al., (1991), "The Use of Sesame Oil and Other Vegetable Oils in the Inhibition of Human Colon Cancer Growth in Vitro", *Anticancer Research,* vol. 11, pp. 209–216.

Fink et al., (1990) "Laboratory Models of Sepsis and Septic Shock", *Journal of Surgical Research,* vol. 49, pp. 186–196.

Shimizu et al., (1989), "Production of Dihmo-$\gamma$-linolenic Acid by *Mortierella alpina* 1S-4", JAOCS, vol. 66, No. 2, pp. 237–241.

Baker et al., (1983), "Evaluation of factors affecting mortality rate after sepsis in a murine cecal ligation and puncture model", *Surgery,* vol. Aug. 1983, pp. 331–335.

ENTERAL FORMULATIONS FOR TREATMENT OF INFLAMMATION AND INFECTION

REFERENCE TO RELATED APPLICATIONS

The present application is a continuation-in-part of U.S. patent application Ser. No. 08/201,682, entitled "Anti-inflammatory and Infection Protective Effects of Sesamin-Based Lignans", filed Feb. 25, 1994, on an application of the presents inventors, the disclosure of which is incorporated herein by reference.

BACKGROUND OF THE INVENTION

The present invention relates to dietary manipulation for the treatment of disease. More particularly, the present invention relates to the use saponins in an enteral formulation for treatment of infection and inflammation.

The last decade has seen an explosion in the exploration of the interaction between diet and disease. In particular, the effects of various amino acids and lipids in the diet on a variety of conditions including heart disease, hypercatabolic states, liver disease, immunosupresssion, and infection treatment have been uncovered. Often, the effects are far removed from the norm and as such are unexpected. One of the most important developments of this type has been the discovery that by changing the dietary lipid content, positive effects in health treatment beyond plasma fat modification could be achieved. While the early work in modifying lipid content and type in diet came from an understanding that saturated fats cause particular problems in heart disease, later work determined that not just the use of polyunsaturated fats but also the type of polyunsaturated fat was important.

There are three major families of polyunsaturated fatty acids: $\omega 3$, $\omega 6$ and $\omega 9$. The names are based on location of the closest double bonds to the methyl end of the fatty acid; that is, if the closest double bond is between the third and fourth carbon atoms from the methyl group, the molecule is classified as an $\omega 3$ fatty acid while if the double bond is between the 6th and 7th carbon atoms, it is classified as an $\omega 6$ fatty acid. Mammals can desaturate or elongate fatty acid chains but cannot interconvert fatty acids from one family to another. The most important dietary fatty acids are the $C_{18}$ and $C_{20}$ fatty acids, primarily linoleic (C18:2$\omega$6), linolenic acid (C18:3$\omega$3), $\gamma$-linolenic acid (C18:3$\omega$6) and dihomo-$\gamma$linolenic acid (C20:3$\omega$6). Manipulation of the content of these fatty acids changes the ratio of arachidonic, eicosapentanoic, and decahexanoic acids (C20:4$\omega$6, C20:5$\omega$3, and C22:6$\omega$receptively) and can cause far reaching effects in terms of immunosuppression, response to hypercatabolic states, and infection. For example, U.S. Pat. No. 4,752,618, issued Jun. 21, 1988 on an application of Mascioli et al., the disclosure of which is incorporated herein by reference, discloses the beneficial effects of $\omega 3$ fatty acids in the treatment of infection. In U.S. Pat. No. 5,260,336, issued Nov. 3, 1993 on an application of Forse et al., the disclosure of which is also incorporated herein by reference, concerns a method of minimizing the effect of catabolic illness or infection using an oil such as olive oil which is rich in $\omega 9$ fatty acids. Other similar patents and articles, such as U.S. Pat. No. 4,810,726, issued. Mar. 7, 1989 on an application of Bistrian et al., the disclosure of which is also incorporated herein by reference, disclose other means of treating illness using fatty acid dietary manipulation.

The "culprit" in many diets appears to be the high level of $\omega 6$ fatty acids, primarily linoleic acid, a precursor for the formation of arachidonic acid which is a substrate for the production of pro inflammatory dienoic eicosanoids including $PGE_2$ and $TxA_2$ which can lead to elevated levels of thromboxane $A_2$ and related prostanoids. Elevation of these prostanoids has been linked to problems in response to endotoxin challenge and other infection states. Accordingly, the new wave in diets has been to minimize the $\omega 6$ fatty acid content (which, although an essential fatty acid, is not needed in the quantities found in most commercial oils) while maximizing the $\omega 3$ fatty acids (e.g., fish oil) and $\omega 9$ fatty acids (e.g., olive oil). Similarly, although sesame oil has long been promoted as having medicinal benefits, it is only recently that the effects have been traced to sesamin (and its related lignans) in the sesame oil. In fact, U.S. patent application Ser. No. 08/201,682, filed Feb. 25, 1994, on an application of the same inventors, discloses that sesamin can promote resistance to infection and reduce inflammation. Thus, materials which modify lipid content in the diet may have important and surprising health effects.

The present invention uses saponins to treat infection and reduce inflammation. It has also been found that these saponins can work in concert with other agents such as fish oils to provide quicker (and consequently better) protection against infection.

Saponins are surface active triterpene or sterol glycosides. Although the saponins are found mainly in plants, they have also been found in certain marine animals such as echinoderms like starfish and sea cucumbers. Most saponins are non-toxic when taken orally, but many are toxic upon i.m. or i.v. injection. Saponins are most often ingested by man in legumes such as chick peas and soy beans. In fact, it has been theorized that legumes rich in saponins may reduce the threat of heart disease based, in part, on the finding that saponins can reduce plasma cholesterol levels in animals. See, e.g., Newman et al., *Poultry Science* 37 42–45(1957).

However, the main medicinal use for saponins appears to be their properties as immunostimulating substances or adjuvants. Reports of immunopotentiating advantages using saponins go back over fifty years (see, e.g., Thibault and Richou, *C.R. Soc. Biol.* 121 718–721 (1936)). While saponins are available from many sources, much of the work on immunostimulation has used saponins derived from the inner bark of the South American soaptree, Quillaja saponaria Molina. These saponins, normally designated as the Quill A saponins, remain the principal medicinal saponins in use today.

Although many other medicinal uses have been hypothesized for saponins, there has been no systematic proof that any effects other than use as an adjuvant is medicinally feasible. However, saponins have been found in some plants used in traditional or folk remedies. For example, saponins are present in ginseng which has long been used in Asia for treatment of a variety of conditions. Similarly, other homeopathic remedies also may contain saponins. The recent interest in homeopathic remedies has lead to a further exploration of the properties of materials such as saponins.

Accordingly, an object of the invention is to provide an enteral dietary supplement containing saponins.

Another object of the invention is to provide a means of treating infection and/or inflammation using saponins.

A further object of the invention is to provide a dietary supplement useful in improving the effects of $\omega 3$ fatty acids on treatment of infection.

An additional object of the invention is to provide a dietary supplement useful in improving the uptake of polyunsaturated fatty acids (e.g., EPA and DHA) in tissue.

A still further object of the invention is to provide a method of treating infection and/or inflammation using dietary manipulation.

These and other objects and features of the invention will be apparent from the following description and the claims.

SUMMARY OF THE INVENTION

The present invention features enteral formulations for treatment of inflammation and infections, as well as methods of treatment itself. These formulations are based on the surprising properties of saponins, a material that is often used as an adjuvant but not as the medicament itself. The saponins are effective with standard enteral formulations such as safflower oil dietary supplements and appear to have additive, or even synergistic, effects with $\omega 3$ fatty acid formulations such as those derived from fish oil or linseed oil. The saponins can also be used with sesamin and related lignans from sesame oil to provide particularly advantageous diets. These saponins could also be included in other food products such as margarines and butter as well as dietary supplements. Such other food products and dietary supplements are included in the enteral formulations herein.

More particularly, the present invention features an enteral formulation adapted for treatment of infection or inflammation in a patient which includes an effective amount of a saponin as an active ingredient. The term "effective amount" means a sufficient amount of the saponin to cause the clinical effect in terms of anti-inflammation and/or anti-infection properties. This effective amount can vary due to a number of factors including type of saponin and personal metabolism. For Quill A, one of the most readily available saponins, this effective amount appears to be about 0.1% -1.0% by weight of the enteral diet, with a 0.25% amount being preferred. For other saponins, with different purification and potency, different effective amounts may easily be determined.

The enteral formulation useful in the invention may include particular fatty acids or other materials which have similar anti-inflammatory properties. For example, the previously cited U.S. Pat. No. 4,752,618 discloses that $\omega 3$ fatty acids may have anti-infection properties. An enteral formulation which includes these $\omega 3$ fatty acids in conjunction with the saponins is, therefore, advantageous. Preferred sources of $\omega 3$ are the fish oils, and linseed (flax) oil, most preferably the oils derived from cold water fish which have at least 10% of their lipid content in $\omega 3$ fatty acids and flax oil which contains approximately 55% linolenic acid (18:3 $\omega 3$). Examples of the useful cold water fish include menhaden and sardine. In fact, as is shown later in the examples, the addition of saponins to an enteral formulation containing $\omega 3$ fatty acids causes less lagtime until the beneficial effects of the $\omega 3$ fatty acids occur and increased uptake of $\omega 3$ fatty acids into tissue. These saponins may also yield beneficial effects with other dietary oils such as borage oil, black currant seed oil, canola oil, and rapeseed oil.

Another additive useful in an enteral formulation is a lignan of the sesamin family. Previously cited U.S. patent application Ser. No. 08/201,682 discloses the anti-infection and anti-inflammatory properties of these lignans. The lignans preferred include sesamin, episesamin, sesaminol, espisemsaminol, and sesamolin. A combination therapy including these lignans and the saponins may be particularly advantageous.

Any enteral formulation preferably includes essential amino acids, essential fatty acids, and/or essential vitamins and minerals. The enteral formulations of the present invention may be in the form of a dietary supplement or used as a total enteral feeding regimen. If the later, these essential nutrients are required while even in a supplement, the addition insures that the patient is obtaining these nutrients.

The enteral formulation such as is previously described are particularly useful in treating infection and inflammation. In fact, these formulations may be used in at risk patients to prevent possible infection or inflammation. Further, when used with the other formulations such as the $\omega 3$ fatty acids, the time to effective action may be reduced.

The following description and non-limiting examples further elucidate the invention.

DETAILED DESCRIPTION

The present invention provides an enteral formulation useful in treating inflammation and/or infection. This enteral formulation includes an effective amount of a saponin such as Quill A, possible in conjunction with a diet rich in $\omega 3$ fatty acids or a diet containing a lignan such as sesamin. As such, saponins show remarkable promise as additives in treating infection states, particularly acute infections e.g., sepsis.

The following examples, which all use saponins in enteral diets, further explain the invention.

EXAMPLE 1

This example explains the procedure used to create the diets used for test purposes. The two diets basic diets were made, a safflower oil diet (SO) which had large quantities of $\omega 6$ fatty acids, primarily in the form of linoleic acid, and a fish oil (FO) diet which had a large percentage of $\omega 3$ fatty acids. The oil portion of the safflower oil diet was made by taking 52 g of safflower oil (SVO Specialty Products, Culberton, Mont.) and mixing it with 88 g of palm oil and 10 g of Trisum, a high oleic sunflower oil. The fish oil diet used menhaden oil, which has 32% $\omega 3$ polyunsaturated fats, primarily in the form of eicosapentanoic acid (EPA) and docosahexaenoic acid (DHA), as the fish oil. The fish oil portion of the fish oil diet was made by blending 8 g safflower oil, 125 g of fish oil, 35 g of palm oil and 10 g of Trisum. These physical mixtures of oils were prepared to maintain the saturated, monounsaturated, and polyunsaturated fat contents identical in both experimental diets. However, the polyunsaturated fatty acids in the former is $\omega 6$ type and in the latter is $\omega 3$. One hundred fifty grams of each oil mixture was added to 850 g of AIN-76, a fat-free basal diet which contained essential minerals and vitamins. For each 1000 g of either enteral diet, 15% by weight was in form of fat with the fat calories being approximately 30% of the total (as recommended by the Surgeon General).

The combination of the fat and the AIN-76 fat-free basal diet had 0.05% t-butyl hydroxy tolulene added as an antioxidant, and the diets were stored in individual daily rations, flushed with nitrogen to minimize oxidation, at 4° C. The animals were fed ad libium every day before dusk.

Separate groups of Balb/c mice were maintained on the safflower oil diet, the fish oil diet, and the two diets supplemented with saponins. Plasma was sampled at 4, 7 and 10 days and the fatty acid compositions of phospholipids in the plasma were determined by gas chromatography following a thin layer of chromatography.

The relative mole percent of individual fatty acids (including linoleic acid and arachidonic acid) incorporated into the plasma phospholipids and the tissues were determined. There was substantially no difference in the fatty acid pattern for the safflower oil diet vs. the safflower oil with saponin diet but the fish oil diet vs. fish oil with saponin diet was another matter. At day 4, the relative percentages of eicosapentanoid acid and decahexenoic acid (DHA) were twice as high in the plasma phospholipids of mice consuming the fish oil with saponins diet as compared with the fish oil alone. By day 7, the differences disappeared. However, the levels of tissue polyunsaturated $\omega 3$ fatty acids increased at day 7 and remained elevated until day 10.

EXAMPLE 2

In this example, Balb/C mice were maintained ad libium on one of the diets described in Example 1, the safflower oil diet, for three weeks. Safflower oil diets are commonly used for enteral nutrition. A first group received just the safflower oil diet (SO) while the second group had the safflower oil diet supplemented with 0.25% saponins (SO+). There were twenty animals in the first group and seventeen in the second group.

At the end of three weeks, all the animals in both groups underwent cecal ligation and puncture. To perform this procedure, the mice were anaesthetized and then shaved over the anterior abdominal wall. A midline incision, approximately 2 cm long, was made, sufficient to expose the cecum and adjacent intestine. With a 3-0 silk suture, the cecum was tightly ligated at its base without causing bowel obstruction. The cecum was then punctured twice with a 22 gauge needle, gently squeezed to exude feces and to insure that the two puncture holes did not close. The abdominal incision was then closed and 1 ml of saline was administered subcutaneously for fluid resuscitation. This cecal ligation and puncture is a widely accepted form of infection model to resemble abdominal sepsis. See, e.g., C. Baker et al., "Evaluation of factors affecting mortality rate after sepsis in a murine cecal ligation and puncture model," Surgery (August 1983), pp. 331-335. Survival of the mice is the normal measure of treatment effectiveness.

In addition, ten animals were fed each diet to serve as controls and were a sham operated; this means, that the abdominal operation was performed but cecal ligation and puncture was not carried out.

TABLE 1

| Diets | 24 hours | 48 hours | 72 hours | 96 hours |
|---|---|---|---|---|
| SAFFLOWER OIL (SO) | 20 (100) | 14 (70) | 6 (30)* | 4 (20)* |
| SAFFLOWER OIL + SAPONINS | 17 (100) | 16 (94) | 15 (88)** | 15 (88)** |

TABLE 1-continued

| Diets | 24 hours | 48 hours | 72 hours | 96 hours |
|---|---|---|---|---|
| (SO+) | | | | |

Table 1 shows the survival on the SO diet vs. the SO+ diet. While all the animals in each group were alive at 24 hours, the number of animals alive at 48, 72 and 96 hours decreases rapidly for the safflower oil group while the group being treated with the safflower plus saponin diet shows very little mortality. The first number is the number of animals remaining alive while the second is a percent remaining alive. At 72 hours, the number of animals surviving is statistically significant ($p<0.05$ using a student t test) while at 96 hours, the data are even better ($p<0.01$). The groups of animals consuming the diets supplemented with saponins showed no mortality.

Accordingly, this shows that adding the saponins to a safflower oil diet has significant anti-infection effects.

EXAMPLE 3

The beneficial effects of feeding diets enriched with safflower oil (15 wt %=30% total calories) supplemented with or without saponins (0.25%) was tested in an infection model. Groups of 10 female Balb/c mice, 6-8 weeks old, were fed the two diets for 3 weeks. The plasma levels of thrombxane $B_2$ (TBX2), tumor necrosis factor (TNF)-$\alpha$ and other proinflammatory mediators were determined in plasma 90 minutes after an interperitonial injection of lipopolysacchride (LPS) (20mg/kg).

TABLE 2

| | SAFFLOWER OIL (SO) | SO + SAPONINS |
|---|---|---|
| TXB$_2$ (pg/ml*) | 466 ± 98 | 257 ± 48# |
| TNF-$\alpha$ (pg/ml*) | 380 ± 100 | 100 ± 40# |

*means ± S.D of determinations following LPS i.p injection in mice (n = 10 in each group.)
p < 0.05.

The increase in survival of animals in Example 2 were associated with significantly lower concentrations (45%) of the LPS-induced TBX$_2$ and TNF-$\alpha$ in the circulation while the AA content, a 5precursor for the formation of dienoic eicosanoids (such as TBX$_2$), was unchanged for the groups of mice fed safflower oil diets containing saponins as described in Example 1. These data suggest that saponins possess anti-inflammatory properties which may include inhibiting the activities of phospholipase A$_2$ or cyclooxygenase enzymes. Further, the ability of saponins to markedly lower (74%) the LPS-induced in vivo production of TNF-$\alpha$ suggests a possible mechanism by which dietary saponins confer protection against infection irrespective of the type of polyunsaturated fatty acid in the diet. These data indicate that inclusion of saponins in an enteral formulation containing different types of polyunsaturated fatty acids ($\omega 3$, $\omega 6$, or $\omega 9$) could benefit critically ill patients.

EXAMPLE 4

In this experiment, Balb/c mice were again maintained on either the safflower oil diet alone or the safflower oil diet supplemented with 0.25% of the saponin Quill A. Spleens were isolated aseptically at 1, 2 and 3 weeks and single cell suspensions were prepared. One million spleen cells were stimulated with either concanavalin A (Con A-1 mg/ml) or lyopopolysacchride (lps-10 μg/ml) for twenty-four hours, both of which are known to induce the production of proinflammatory mediators. Cell free supernatants were collected and the amounts of prostaglandin $E_2$ (PGE2) were determined by immunoassay. The $PGE_2$ levels in the supernatants from the spleen cells of the animals treated with the saponins were significantly lower (see Table 2) than those with the safflower oil diet alone on day 7 ($p<0.05$). After two or three weeks of feeding, the mean concentrations of the $PGE_2$ were not significantly different. These data suggest the saponins exhibited anti-inflammatory properties and that feeding safflower oil diets with saponins may have selected a cell population which participated in defending the host against infection.

TABLE 3

|  | Con A | LPS |
|---|---|---|
| SAFFLOWER OIL (SO) | 114 ± 20 | 248 ± 32 |
| SAFFLOWER OIL + SAPONINS (SO+) | 70 ± 13 | 153 ± 11 |

All valves in pg/ml at day 7.

Since it is known that fish oil diets will provide anti-infection properties, the ability of the saponin addition to provide a more rapid incorporation of $\omega 3$ fatty acids in the fatty acid profiles of the phospholipids in the plasma and in the tissues suggest that this may speed the action of the fish oil. If so, this effect may be important in treating infection, particularly with post-operative patients.

The foregoing examples are merely exemplary and one skilled in the art may determine other enteral diets and methods of treatment using such an enteral diet which falls within the scope of the present invention. The invention is defined not by these examples but rather by the following claims.

What is claimed is:

1. An enteral formulation for the treatment of infection or inflammation in a patient having as an active ingredient an effective amount of Quil A saponin, said enteral formulation further comprising a source of dietary polyunsaturated fatty acids, said fatty acids forming at least significant part of the fat content given to said patient.

2. The enteral formulation of claim 1 wherein said source of dietary polyunsaturated fatty acids is selected from the group consisting of fish oils and vegetable oils rich in $\omega 3$ fatty acids.

3. The enteral formulation of claim 2 wherein said source of $\omega 3$ fatty acids is a fish oil selected from the group consisting of fish oils having at least 10% of the lipid content as $\omega 3$ fatty acids.

4. The enteral formulation of claim 1 further comprising a lignan selected from the group consisting of sesamin, episesamin, sesaminol, episesaminol, and sesamolin.

5. The enteral formulation of claim 4 wherein said lignan is added to said enteral formulation in the form of sesame oil.

6. The enteral formulation of claim 4 wherein said lignan is added to said enteral formulation in the form of purified lignan.

7. The enteral formulation of claim 1 :further comprising essential amino acids.

8. The enteral formulation of claim 1 further comprising essential vitamins and minerals.

9. The enteral formulation of claim 1 wherein said enteral formulation includes a dietary oil selected from the group consisting of borage oil, black currant seed oil, canola oil and rapeseed oil.

10. A method of treating infection and preventing infection in at risk persons comprising the step of enteral administration thereto of an effective amount of an enteral formulation in conjunction with a source of dietary polyunsaturated fatty acids which constitute at least a significant part of the fat fed to such persons, said enteral formulation having as its active ingredient Quil A saponin.

11. The method of claim 10 wherein said source of dietary polyunsaturated fatty acids is selected from the group consisting of fish oils and vegetable oils rich in $\omega 3$ fatty acids.

12. The method of claim 11 wherein said source of $\omega 3$ fatty acids is a fish oil selected from the group of fish oils having at least 10% of its lipid content as $\omega 3$ fatty acids.

13. The method of claim 10 wherein said administration step comprises administration of a lignan selected from the group consisting of sesamin, episesamin, sesaminol, episesaminol, and sesamolin in conjunction with said enteral formulation.

14. The method of claim 13 wherein said lignan is added to said enteral formulation in the form of sesame oil.

15. The method of claim 13 wherein said lignan is added to said enteral formulation in the form of a purified lignan.

16. The method of claim 10 wherein said administration step comprises administration of an oil selected from the group consisting of borage oil, black currant seed oil, canola oil, and rapeseed oil in conjunction with said saponin.

* * * * *